(12) United States Patent
Van Abeelen et al.

(10) Patent No.: US 12,128,575 B2
(45) Date of Patent: Oct. 29, 2024

(54) DETERMINING A LOCATION OF A DEVICE

(71) Applicant: KONINKLIJKE PHILIPS N.V., Eindhoven (NL)

(72) Inventors: Frank Anton Van Abeelen, Eindhoven (NL); Yannyk Parulian Julian Bourquin, Eindhoven (NL); Karel Johannes Adrianus Van Den Aker, Liempde (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 394 days.

(21) Appl. No.: 17/762,108

(22) PCT Filed: Sep. 29, 2020

(86) PCT No.: PCT/EP2020/077161
§ 371 (c)(1),
(2) Date: Mar. 21, 2022

(87) PCT Pub. No.: WO2021/063906
PCT Pub. Date: Apr. 8, 2021

(65) Prior Publication Data
US 2022/0347871 A1 Nov. 3, 2022

(30) Foreign Application Priority Data
Oct. 2, 2019 (EP) .................................. 19201177

(51) Int. Cl.
*B26B 19/00* (2006.01)
*B26B 19/38* (2006.01)
*G06T 7/00* (2017.01)

(52) U.S. Cl.
CPC .......... *B26B 19/388* (2013.01); *G06T 7/0012* (2013.01); *G06T 2207/30088* (2013.01)

(58) Field of Classification Search
None
See application file for complete search history.

(56) References Cited

U.S. PATENT DOCUMENTS

| 2011/0144779 A1* | 6/2011 | Janse | H04M 1/026 700/94 |
| 2014/0137883 A1* | 5/2014 | Rothschild | B26B 19/388 132/200 |

(Continued)

FOREIGN PATENT DOCUMENTS

| EP | 3363606 A1 | 8/2018 |
| EP | 3528091 A1 | 8/2019 |

(Continued)

OTHER PUBLICATIONS

International Search Report and Written Opinion Dated Dec. 3, 2020 For International Application No. PCT/EP2020/077161 Filed Sep. 29, 2020.

*Primary Examiner* — Paul B Yanchus, III

(57) ABSTRACT

A computer-implemented method of determining a location of a personal care device with respect to a skin surface of a subject, the personal care device being configured to perform a personal care treatment to the skin when in contact with the skin surface. The method includes receiving data representative of a measured degree of curvature of the skin surface within a first region of the skin surface of the subject, with which the personal care device is in contact; determining, by comparing the measured degree of curvature with curvature information for a plurality of regions of the skin surface of the subject contained in a database, an indication of a location of the first region of the skin surface on the subject; and performing, based on the determined indication of the location of the first region, an action in respect of the (Continued)

personal care device. A processing apparatus, a system, a personal care device, and a computer program product are also disclosed.

15 Claims, 13 Drawing Sheets

(56) References Cited

U.S. PATENT DOCUMENTS

2016/0257009 A1 9/2016 Godlieb
2016/0297085 A1 10/2016 Uit De Bulten
2018/0204346 A1 7/2018 Van Bree

FOREIGN PATENT DOCUMENTS

WO 2015068068 A1 5/2015
WO 2018069265 A1 4/2018

* cited by examiner

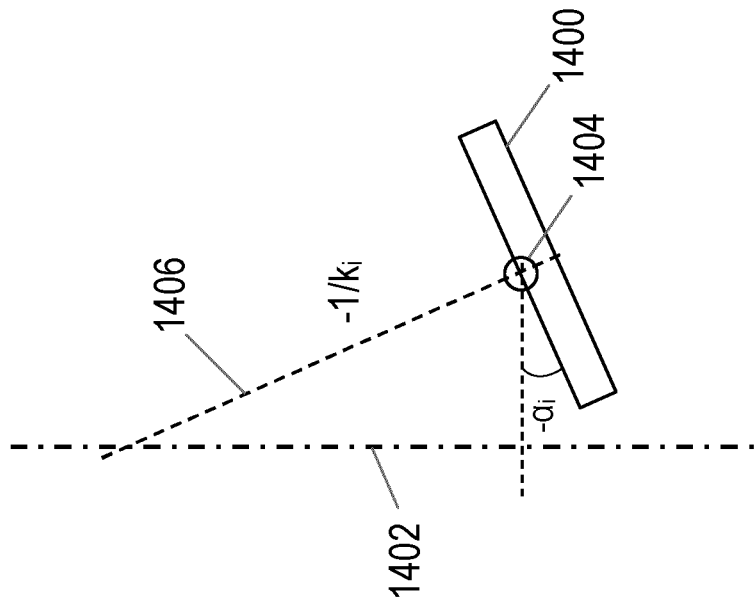
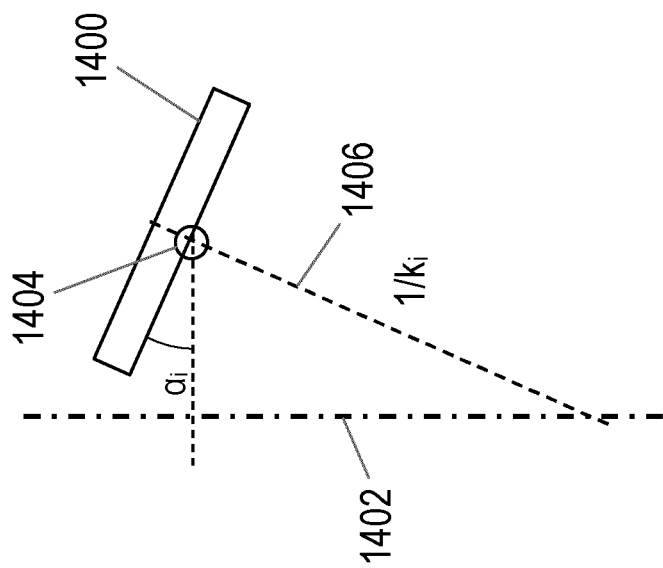

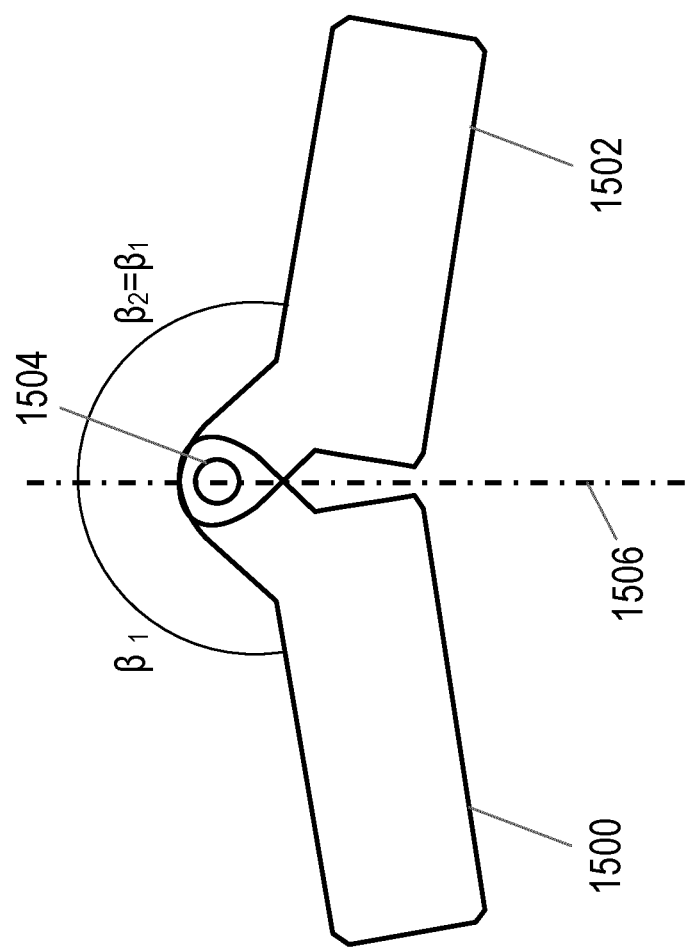

DETERMINING A LOCATION OF A DEVICE

CROSS REFERENCE TO RELATED APPLICATIONS

This application is the U.S. National Phase application under 35 U.S.C. § 371 of International Application No. PCT/EP2020/077161 filed Sep. 29, 2020, which claims the benefit of European Patent Application Number 19201177.3 filed Oct. 2, 2019. These applications are hereby incorporated by reference herein.

FIELD OF THE INVENTION

The invention relates to methods, apparatuses and systems for determining a location of a device and, in particular, of determining a location of a personal care device with respect to a surface of a subject's skin.

BACKGROUND OF THE INVENTION

Personal care devices are used to perform personal care activities on skin of a user. Such personal care activities include, but are not limited to, epilating, hair care activities, such as shaving and trimming, or massaging. While the user may know which part of his or her body is being treated by the personal care device, and may be able to tailor the application of the personal care accordingly, the device itself may function in a suboptimal manner for some parts of the body compared to others.

EP 3 528 091 A1 discloses an apparatus for determining a location of a personal care device on a user. The apparatus comprises a processor configured to detect a location of one or more parts of the body of a user, detect motions of at least one of the parts of the body of the user induced by the personal care device when the personal care device is in use, and determine the location of the personal care device on the user based on the detected motions of the at least one part of the body of the user in relation to the detected location of the at least one part of the body of the user.

SUMMARY OF THE INVENTION

In order to operate in an improved or optimal manner, it can be beneficial for a personal care device to identify its approximate position on the body of a user/subject, for example by identifying a portion of the subject's skin to which the personal care activity is being performed. Existing means for determining a location of a device can be ineffective. Therefore, there is a desire for a more effective means for determining an indication of a location of a device with respect to a skin surface of a subject.

The inventors of the present disclosure have recognized that a location of a personal care device may be determined based on a measured degree of curvature of the surface in respect of which the device is being used. For example, it is possible to determine the location of a personal care device relative to a subject's body by measuring the curvature of a region of the body with which the device is in contact and, based on the measured degree of curvature, determining a part of region of a body having a corresponding curvature.

With knowledge of the body part or region in respect of which the device is being used, appropriate action may be taken to improve the performance of the device, for example by adjusting operating parameters of the device so that it operates in a manner more appropriate for the body part where it is being used, analyzing a personal care routine, tracking skin parameters over time, or providing feedback regarding the personal care activity.

According to a first aspect, there is provided a computer-implemented method of determining a location of a personal care device with respect to a skin surface of a subject. The method comprises receiving data representative of a measured degree of curvature of the skin surface within a first region of the skin surface of the subject, with which the personal care device is in contact; determining, by comparing the measured degree of curvature with curvature information for a plurality of regions of the skin surface of the subject contained in a database, an indication of a location of the first region of the skin surface on the subject; and performing, based on the determined indication of the location of the first region, an action in respect of the personal care device.

Using previously-acquired data regarding the curvature of different parts of a subject's skin surface, a determination may be made of the location of the personal care device based on curvature measurements made while the device is in use. In this way, the device location can be easily determined, such that appropriate actions may be taken based on the determined location.

In some embodiments, the method may further comprise receiving data indicative of a measured displacement of the personal care device between the first region of the skin surface and a second region of the skin surface, with which the personal care device was previously in contact. Determining the indication of the location of the first region may be based further on comparing the data indicative of the measured displacement with position information for the plurality of regions of the skin surface of the subject contained in the database.

The method may, in some embodiments, further comprise, prior to receiving the data representative of the measured degree of curvature of the skin surface within the first region of the skin surface: receiving calibration displacement data indicative of a measured displacement of the personal care device between a plurality of regions of the skin surface of the subject; fitting a computer model of the skin surface of the subject to the received calibration displacement data; determining, from the calibration displacement data and the fitted computer model, curvature information for each region of the plurality of regions; and storing, in the database, the determined curvature information in association with the corresponding region on the skin surface of the subject. This may be considered to be a calibration process.

According to a second aspect, there is provided a processing apparatus configured for determining a location of a personal care device with respect to a skin surface of a subject, the processing apparatus being configured to: receive data representative of a measured degree of curvature of the skin surface within a first region of the skin surface of the subject, with which the personal care device is in contact; retrieve, from a storage medium, curvature information for a plurality of regions of the skin surface of the subject; determine, by comparing the measured degree of curvature with the curvature information for the plurality of regions of the skin surface, a location of the first region of the skin surface on the subject; and generate, based on the determined location of the first region, an instruction of an action to be performed in respect of the personal care device.

According to a third aspect, there is provided a system for determining a location of a personal care device with respect to a skin surface of a subject, the system comprising: a housing to house a communication unit; a skin surface curvature measurement mechanism coupled to the housing, the skin surface curvature measurement mechanism being configured for measuring a degree of curvature of the skin surface of the subject within a first region of the skin surface; and a processing apparatus as discussed herein. The skin surface curvature measurement mechanism is configured to generate the data representative of the measured degree of curvature of the skin surface within the first region of the skin surface. The communication unit is configured to communicate the data representative of the measured degree of curvature of the skin surface within the first region of the skin surface to the processing apparatus.

In some embodiments, the skin surface curvature measurement mechanism may comprise an imaging device configured to acquire image data in respect of the first region of the skin surface. The processing apparatus may be further configured to determine the degree of curvature of the skin surface within the first region of the skin surface using the acquired image data.

The skin surface curvature measurement mechanism may, in some embodiments, comprise a first surface-engaging element and a second surface-engaging element, the first and second surface-engaging elements being moveable relative to one another. The data representative of the measured degree of curvature of the skin surface within the first region of the skin surface may comprise a measure of a relative orientation of the first surface-engaging element and second surface-engaging element.

In some embodiments, the system may further comprise at least one orientation sensor configured for measuring an orientation of the first surface-engaging element relative to the housing, and an orientation of the second surface-engaging element relative to the housing. The data representative of the measured degree of curvature of the skin surface within the first region of the skin surface may comprise a measure of the orientation of the first surface-engaging element relative to the housing, and a measure of the orientation of the second surface-engaging element relative to the housing.

The first surface-engaging element and the second surface-engaging element may be pivotally mounted such that they are each pivotable relative to the housing and relative to one another. The data representative of the measured degree of curvature may comprise an average degree of curvature of the skin surface within the first region.

According to a fourth aspect, there is provided a personal care device comprising: a main body; a skin surface curvature measurement mechanism, the skin surface curvature measurement mechanism being configured for measuring a degree of curvature of the skin surface of the subject within a first region of the skin surface, with which the personal care device is in contact; and a processing apparatus as disclosed herein. The processing apparatus is configured to receive data representative of a measured degree of curvature of the skin surface from the skin surface curvature measurement mechanism.

The personal care device may, in some embodiments, further comprise an attachment to house a communication unit, the attachment being detachably mountable to the main body. The skin surface curvature measurement mechanism may be coupled to the attachment. The main body may accommodate the processing apparatus. The communication unit may be configured to communicate the data representative of the measured degree of curvature of the skin surface to the processing apparatus.

In some embodiments, the personal care device may further comprise a sensor for acquiring motion data for the personal care device. The processing apparatus may be configured to determine the location of the first region of the skin surface on the subject further based on motion data acquired using the sensor. The motion data may, for example, comprise the data indicative of a measured displacement.

The personal care device may further comprise a housing supporting at least a first treatment element and a second treatment element. The first treatment element may comprise a first surface-engaging element, and the second treatment element may comprise a second surface-engaging element, the first surface-engaging element and the second surface-engaging element each being pivotally mounted relative to the housing such that they are pivotable relative to one another. The skin surface curvature measurement mechanism may comprise a first sensor configured to measure an orientation of the first surface-engaging element relative to the housing, and a second sensor configured to measure an orientation of the second surface-engaging element relative to the housing.

In some embodiments, the personal care device may be an electric shaver. The first treatment element and the second treatment element may both comprise a shaving unit having an external cutting member, an internal cutting member movably arranged relative to the external cutting member, and a skin-supporting rim surrounding the external cutting member and pivotally mounted relative to the housing, wherein the first surface-engaging element and the second surface-engaging element comprise the skin-supporting rim of the shaving unit of, respectively, the first treatment element and the second treatment element.

According to a fifth aspect, there is provided a computer program product comprising a non-transitory computer readable medium, the computer readable medium having computer readable code embodied therein, the computer readable code being configured such that, on execution by a suitable computer or processor, the computer or processor is caused to perform steps of the method disclosed herein.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 14A and FIG. 14B are diagrams showing an example of how a curvature may be measured according to various embodiments;

FIG. 15 is a diagram showing a further example of how a curvature may be measured according to various embodiments;

DETAILED DESCRIPTION OF THE EMBODIMENTS

Embodiments of this present disclosure provide a mechanism by which a location of a device relative to a skin surface of a subject with which the device is in contact may be determined. Some embodiments are described in the context of a handheld shaver, the location of which may be determined relative to the region of a subject's body or face where hairs are being trimmed or cut using the shaver. However, it will be appreciated that the invention is not limited to shaving devices, and embodiments described herein may be implemented in a wide range of personal care devices configured to perform a personal care treatment to the skin when in contact with the skin surface. Thus, the personal care device described herein may, for example, comprise a hair removal device, such as an epilator or an intense pulsed light (IPL) device, a hair care device, such as a shaver, clippers, or a hair trimmer, a skin health analysis device, an electric massager, a phototherapy device or a pain relief device. Other personal care devices configured to perform a personal care treatment to the skin when in contact with the skin surface are also envisaged.

Figure 1:
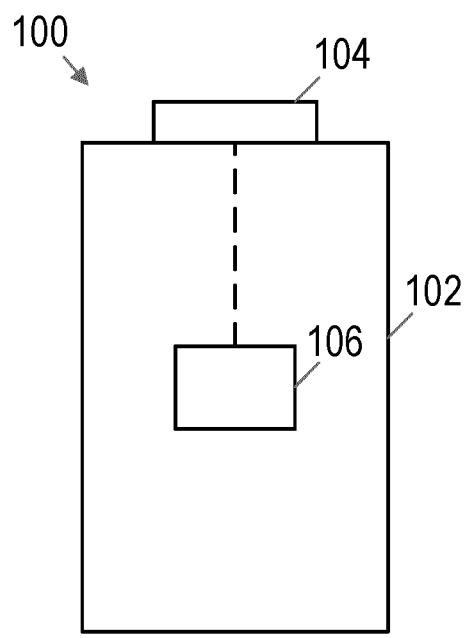
FIG. 1 is a schematic illustration of an example of a personal care device according to various embodiments.

Referring now to the drawings, FIG. 1 is a schematic illustration of an example of a personal care device 100. The personal care device 100 may be intended to be held by a user's hand during use and, as such, may be referred to as a handheld personal care device. The personal care device 100 comprises a main body 102, a skin surface curvature measurement mechanism 104 and a processing apparatus 106. In some embodiments, the personal care device 100 may be formed as an integral device, with its components connected or coupled together in a non-detachable manner. In other embodiments, however, various components of the personal care device 100 may be detachable from other components of the personal care device such that the personal care device is considered to be modular.

The main body 102 may house one or more components of the device. In some examples, the main body may be intended to be held in the user's hand during use.

The skin surface curvature measurement mechanism 104 (also referred to herein as a measurement mechanism 104) is configured for measuring a degree of curvature of the skin surface of the subject within a first region of the skin surface, with which the personal care device is in contact. The measurement mechanism 104 may measure skin surface curvature in a number of ways, as described in greater detail below. The processing apparatus 106 is configured to receive data representative of a measured degree of curvature of the skin surface from the skin surface curvature measurement mechanism 104. The received data may then be processed by the processing mechanism 104 in order to determine a location of the personal care device 100.

The skin surface curvature measurement mechanism 104 may, in some embodiments, comprise a plurality of elements pivotally mounted to a portion of the personal care device 100, such that the plurality of elements are pivotally mounted relative to the personal care device and to one another. The elements may be considered to be surface-engaging elements which, during use, are in contact with the skin surface of the subject. By using a measured orientation of the surface-engaging elements of the skin surface curvature measurement mechanism 104, it is possible to determine a degree of curvature of the skin surface. Thus, a skin surface curvature may be determined for a portion of the skin surface with which that the surface-engaging elements are in contact. As the personal care device 100 is moved over the subject's skin surface, the skin surface curvature may be determined at more positions, and data representing the skin surface curvature may be communicated to the processing apparatus 106 (e.g. by a wired or wireless connection) so that a location of the personal care device can be determined.

Once the data acquired using the skin surface curvature measurement mechanism 104 has been transmitted to the processing apparatus 106, the processing apparatus compares the data with existing curvature information for a plurality of regions of the skin surface of the subject. For example, the processing apparatus 106 may obtain such curvature information from a database or other data structure stored in a storage medium, such as a memory, associated with the personal care device 100. The curvature information may have been acquired and stored in the storage medium as part of a previously-performed calibration process, such that, for a particular subject, curvature information is known for a plurality of regions or locations. By comparing the curvature data measured for a first region of the skin surface on the subject with the stored curvature information, the processing apparatus 106 is able to determine a location of the first region of the skin surface. For example, if the processing apparatus receives data from the skin surface curvature measurement mechanism 104 indicating that the first region has a particular curvature c, it may be determined from the comparison with the stored curvature information that a curvature c corresponds with the chin of the subject. Accordingly it may be determined that the personal care device 100 is in contact with the chin of the subject. Making such a determination can be useful for adjusting a setting or operating parameter of the personal care device 100 to improve the personal care activity. For example, hairs growing from a person's chin are typically coarser than hair growing from a person's cheeks. Therefore, it may be beneficial to increase the speed of a cutting element of a shaver when it is determined that the cutting element of the shaver is positioned at the subject's chin, rather than at the subject's cheeks.

Figure 2:
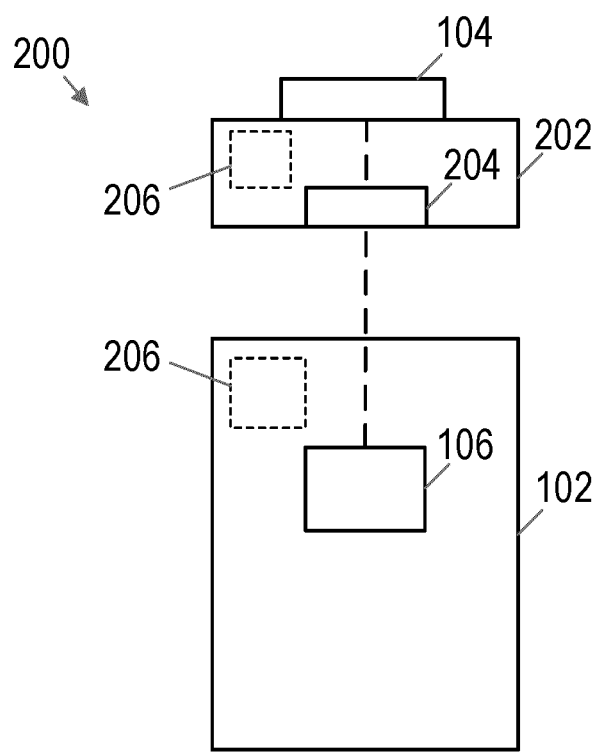
FIG. 2 is a schematic illustration of a further example of a personal care device according to various embodiments.

The embodiment shown in FIG. 1 is formed of a single unit. In other embodiments, the skin surface curvature measurement mechanism 104 may form part of, or be housed by, a separate attachment, which can be removably attached or connected to the main body 102 of the personal care device 100. FIG. 2 is a schematic illustration of an example of a personal care device 200 in which the skin surface curvature measurement mechanism is part of a unit which can be detached from the main body 102. The personal care device 200 includes the main body 102 and the processing apparatus 106 as shown in the example of FIG. 1. However, the personal care device 200 further comprises an attachment 202 to house a communication unit 204, the attachment being detachably mountable to the main body 102. The attachment 202 may be mounted to the main body 102 of the personal care device 200 using attachment mechanisms that will be familiar to those skilled in the art. Enabling the attachment 202 to be removed and reattached to the main body 102 may be beneficial so that the attachment, or components thereof, may be cleaned or easily replaced. For example, an attachment for use in one type of treatment (e.g. shaving) may be removed and replaced with an attachment for use with another type of treatment (e.g. exfoliating).

In the example shown in FIG. 2, the skin surface curvature measurement mechanism 104 is coupled to the attachment 202. In some examples, the measurement mechanism 104 may form part of the attachment 202. The main body 102 accommodates the processing apparatus 106 in this example. However, in other examples, the processing apparatus 106 may be located in the attachment 202 itself.

The communication unit 204 is configured to communicate the data representative of the measured degree of curvature of the skin surface to the processing apparatus 106. Thus, while, in some examples, the data acquired using the skin surface curvature measurement mechanism 104 may be communicated directly from the measurement mechanism to the processing apparatus 106 (as indicated by the dashed line in FIG. 1), in other examples, the data may be communicated to the processing apparatus via the communication unit 204 (as indicated by the dashed lines in FIG. 2).

Complementary electrical connections (not shown) may be provided on the attachment 202 and on the main body 102 where the attachment may be mounted, to facilitate communication of power and/or data between components in the attachment 202 (e.g. the skin surface curvature measurement mechanism 104) and components in the main body 102 (e.g. the processing apparatus 106).

The skin surface curvature measurement mechanism 104 may be able to acquire sufficient curvature data to enable a location of the personal care device 100, 200 to be determined. However, according to some embodiments of the invention, additional data may be acquired and used to determine the location of the personal care device 100, 200 more accurately. In some embodiments, the personal care device 100, 200 may further comprise a sensor 206 for acquiring motion data for the personal care device. The motion data may, for example, comprise data describing how the personal care device has been moved or displaced during a defined measurement period. The processing apparatus 106 may be configured to determine the location of the first region of the skin surface on the subject further based on motion data acquired using the sensor 206, as is described in greater detail below. The sensor 206 may be any sensor capable of measuring, amongst other things, a displacement of the personal care device 100, 200 and or, more specifically, displacement of the skin surface curvature measurement mechanism 104 of the personal care device. In one example, the sensor 206 may comprise an inertial measurement unit (IMU). An IMU, which will be familiar to those skilled in the art, may use an accelerometer, a gyroscope and/or a magnetometer to measure various parameters (e.g. specific force, angular rate and/or orientation) of a device in which the IMU is installed. The sensor 206 may be positioned in the main body 102, or in the attachment 202, as indicated by the use of the dashed lines to represent the sensor in FIG. 2. Data acquired using a sensor 206 is communicated to the processing apparatus 106 via a wired or wireless connection for use in determining the device location. In some embodiments, the data may be communicated from the sensor 206 to the processing apparatus 106 via the electrical connections mentioned above.

In some examples, with the use of a Kalman filter, a gravity vector may be estimated from data acquired using the IMU (e.g. from data acquired using accelerometers in the IMU) along three special axes. The gravity vector may be used (with or without data from a gyroscope of the IMU) to estimate an orientation of the skin surface curvature measurement mechanism 104 with respect to the gravity field, which can help to increase the accuracy of the location determination made by the processing apparatus 106. In some examples, it may be assumed that the part of the subject with which the personal care device is being used is oriented in a particular way during use; for example, it may be assumed that a user's head is upright or slightly tilted during a shaving activity.

Figure 3:
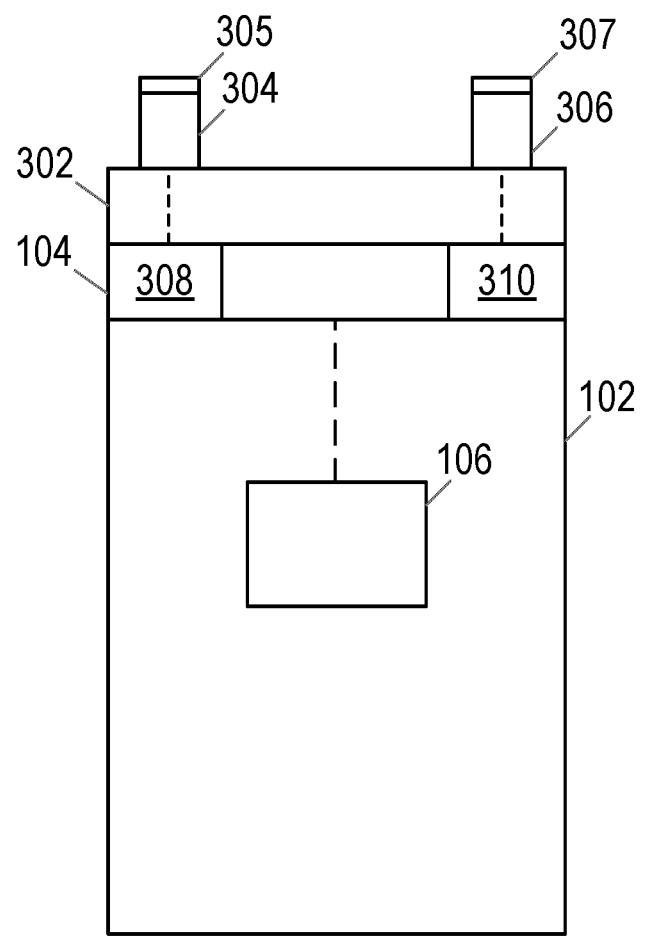
FIG. 3 is a schematic illustration of a further example of a personal care device according to various embodiments.

FIG. 3 is a schematic illustration of a further example of a personal care device 300, according to various embodiments of the invention. The personal care device 300 includes the main body 102, the processing apparatus 106 and the skin surface curvature measurement mechanism 104. The personal care device 300 may further comprise a housing 302 supporting at least a first treatment element 304 and a second treatment element 306. The first treatment 304 may comprise a first surface-engaging element 305, and the second treatment element 306 may comprise a second surface-engaging element 307. Each surface-engaging element 305, 307 is pivotally mounted relative to the housing 302 such that they are pivotable relative to one another. Thus, as the surface-engaging elements 305, 307 engage the skin surface of a subject, each surface-engaging element may independently pivot depending on the curvature of the surface that it contacts. The skin surface curvature measurement mechanism 104 comprises a first sensor 308 configured to measure an orientation of the first surface-engaging element 305 relative to the housing 302, and a second sensor 310 configured to measure an orientation of the second surface-engaging element 307 relative to the housing. The relative orientations of the first and second surface-engaging elements 305, 307 are used by the processing apparatus 106 to determine the location of the first region of the skin surface on the subject, with which the personal care device 300 is in contact.

Figure 4:
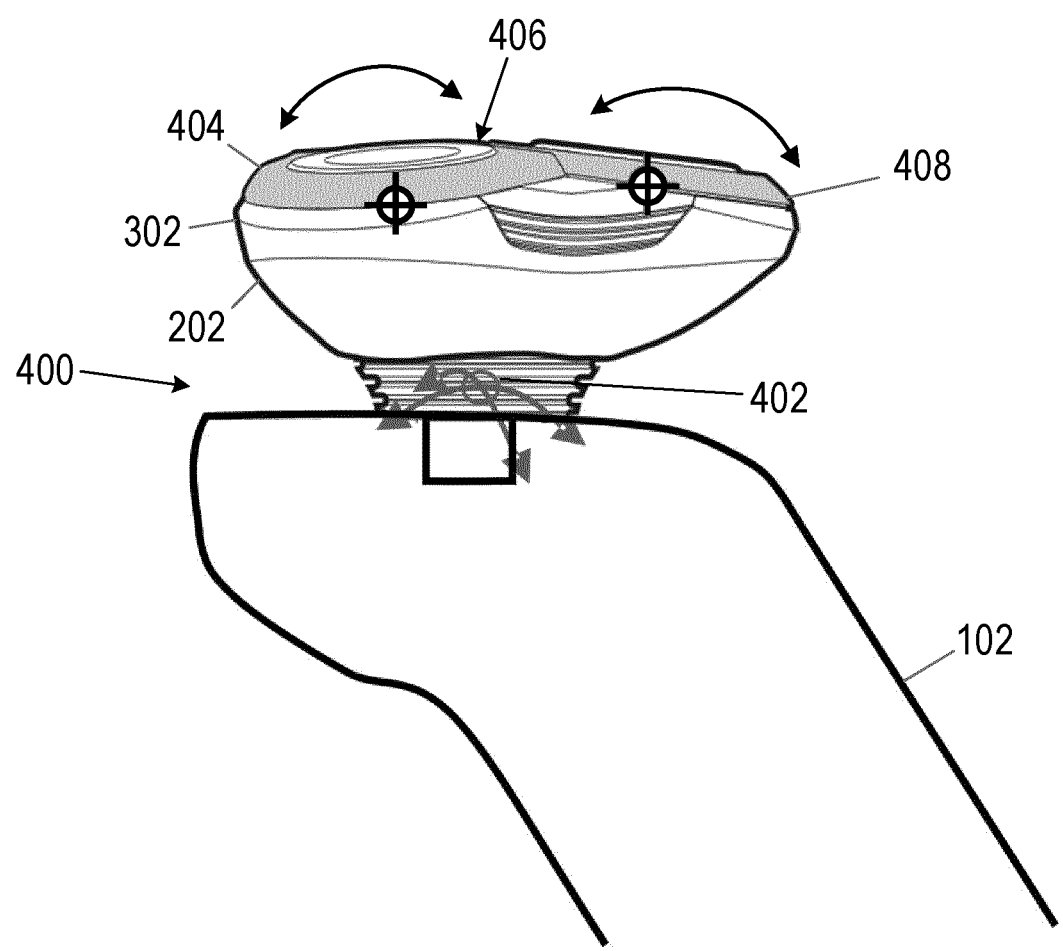
FIG. 4 is an illustration of an example of part of a personal care device according to various embodiments.
Figure 5:
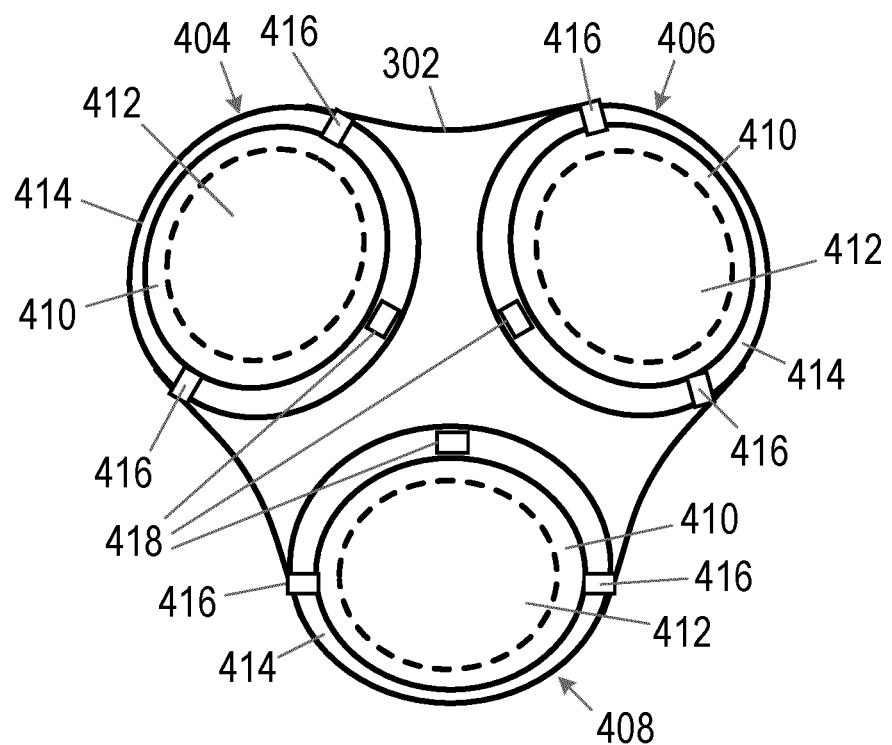
FIG. 5 is a plan view illustration of an example of an attachment of the personal care device of FIG. 4, according to various embodiments.

Specific examples of personal care devices in which the present invention may be embodied are now discussed with reference to FIGS. 4 to 11. FIG. 4 is an illustration of part of a personal care device 400 which, in this example, comprises an electric shaver. In FIG. 4, part of the main body 102 is shown, along with the attachment 202, which is mounted to the main body. FIG. 5 is a plan view illustration of the attachment 202 of FIG. 4. The attachment 202 may be pivotally mounted, such that the attachment may pivot relative to the main body 102 about a pivot point 402. The personal care device 400 also includes the housing 302. In the example shown in FIGS. 4 and 5, the housing 302 supports three treatment elements 404, 406, 408, each of which comprises a shaving unit. In other examples, more or fewer treatment elements may be provided on the attachment 202. The shaving unit of each treatment element 404, 406, 408 has an external cutting member 410 and an internal cutting member 412 movably arranged relative to the external cutting member. The internal cutting member 412 sits underneath the external cutting member 410 and, therefore, may only be visible through slits in the external cutting member. For this reason, the internal cutting member 412 is shown with dashed lines. In some examples, the internal cutting member 412 may rotate relative to (e.g. in an opposite direction to) its corresponding external cutting member 410 to effect cutting of hairs extending from the subject's skin. Each treatment element 404, 406, 408 also includes a skin-supporting rim 414 surrounding the external cutting member 410 and pivotally mounted relative to the housing 302 (about an axes indicated by crosshairs). In this example, the skin-supporting rim 414 of each respective treatment element 404, 406, 408 comprises a surface-engaging element (e.g. the surface engaging elements 305, 307). Thus, in use, the treatment elements 404, 406, 408 of the personal care device 400 are placed against the skin surface of the subject whose hair is to be cut, and the skin-supporting rim 414 is caused to pivot relative to the housing 302 in a manner dependent upon the curvature of the surface of the skin with which the skin-supporting rim is in contact.

The above example, described with reference to FIGS. 4 and 5, relates to an electric shaver having three shaving units. More generally, a personal care device (e.g. the personal care device 300) may be an electric shaver, wherein the first treatment element 304 and the second treatment element 306 both comprise a shaving unit having an external cutting member 410, an internal cutting member 412 movably arranged relative to the external cutting member, and a skin-supporting rim 414 surrounding the external cutting member and pivotally mounted relative to the housing 302, wherein the first surface-engaging element 305 and the second surface-engaging element 307 comprise the skin-supporting rim 414 of the shaving unit of, respectively, the first treatment element 304 and the second treatment element 306.

As noted above, one or more sensors (e.g. the sensors 308, 310) may be used to measure respective orientations of the surface-engaging elements 305, 307, 414 relative to the housing 302, and various techniques may be used to achieve this. In FIG. 5, a pair of fulcrums 416, or pivot points, is shown positioned at opposite sides of each shaving unit and, therefore, each skin-supporting rim 414. Each skin-supporting rim 414 is mounted such that it is able to pivot about an axis defined by the respective pair of fulcrums 416. The orientation of each skin-supporting rim 414 relative to the housing 302 may be measured by detecting contact (or a degree of contact) with an engagement surface 418 positioned beneath one side of skin-supporting rim. Various embodiments of the engagement surface 418 and the interaction of each skin-supporting rim 414 with its corresponding engagement surface are described below with reference to FIGS. 6, 7, 8, 9 and 10.

Figure 6:
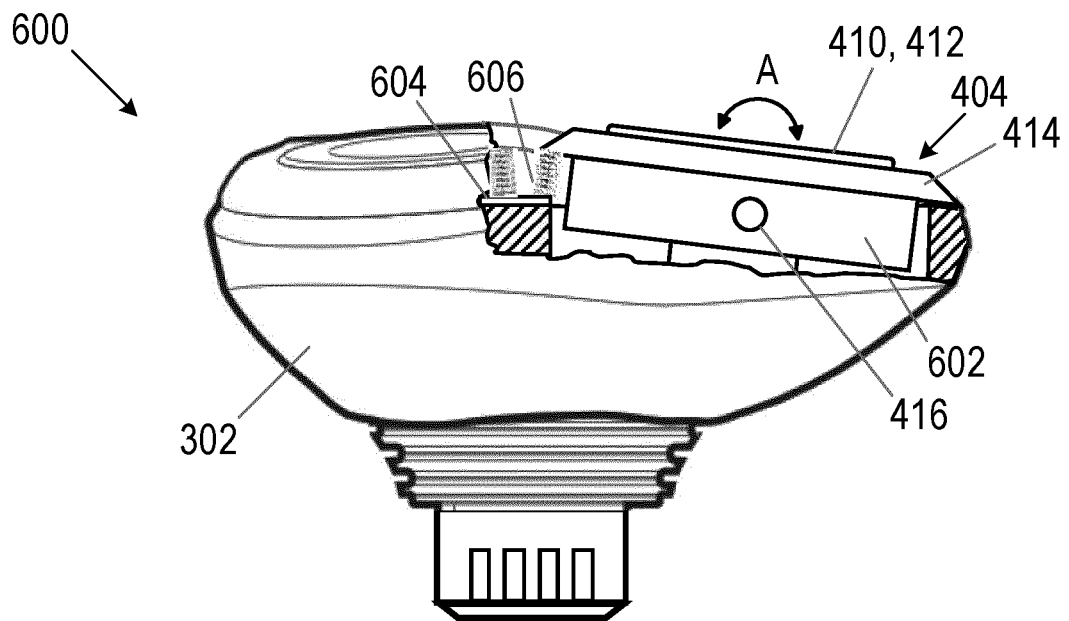
FIG. 6 is a side view illustration of an example of an attachment of a personal care device according to various embodiments.
Figure 7:
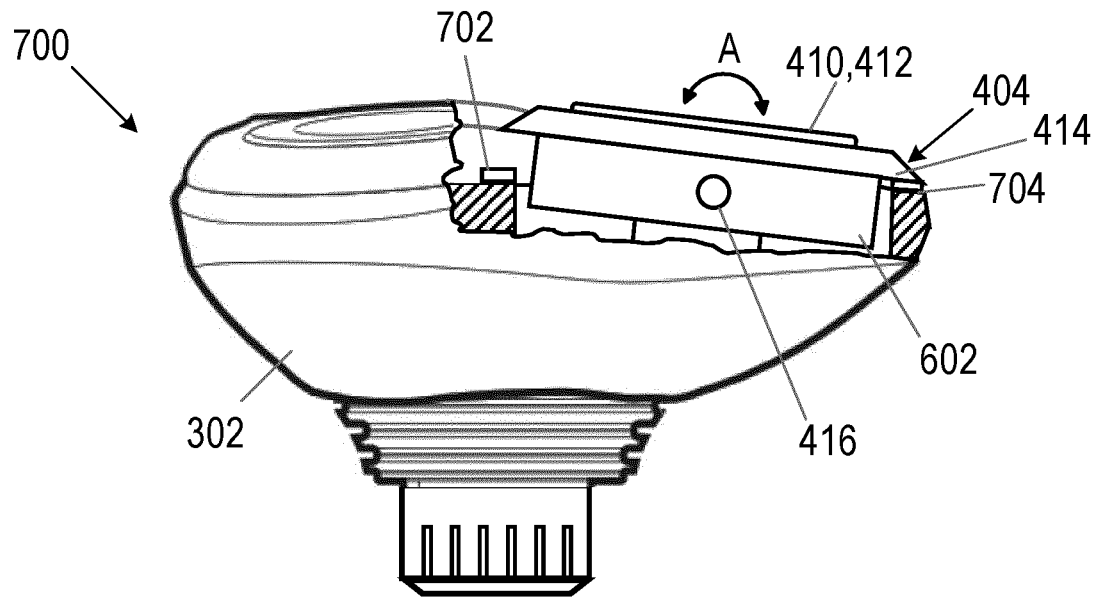
FIG. 7 is a side view illustration of a further example of an attachment of a personal care device according to various embodiments.

FIGS. 6 and 7 are side view illustrations showing attachments 600, 700, respectively, and each having a cutaway section to illustrate the pivotal movement of the surface-engaging elements. In both FIGS. 6 and 7, the cutaway section reveals a treatment element 404, having a shaving unit formed of an internal cutting member 412 and an external cutting member 410 and a skin-supporting rim 414. The skin-supporting rim 414 is attached to (or an extension of) a base 602, via which the skin-supporting rim is pivotally mounted to a fulcrum 416 about which the skin-supporting rim may pivot in the direction indicated by the arrow A. In the embodiments shown in FIGS. 6 and 7, different sensors are used to measure the orientation of the skin-supporting rim 414 relative to the housing 302.

In the attachment 600 of FIG. 6, a multiple-point resistive force sensor 604 is provided for measuring the orientation of the skin-supporting rim 414 relative to the housing 302. In this embodiment, when a force is applied to the side of the skin-supporting rim 414 (e.g. as a result of the skin-supporting rim being pressed against the skin surface of a subject), causing it to pivot towards the force sensor 604, the skin-supporting rim compresses a spring 606, thereby applying a force to the force sensor. When a force is applied by a spring 606 onto the force sensor 604, a resistance within the force sensor changes, and is measured by electronic components (not shown) within the attachment 600 and/or the main body 102 (not shown in FIG. 6). The force applied to the force sensor 604 is proportional to the amount of compression of the spring 606 caused by the skin-supporting rim 414. Each skin-supporting rim 414 is provided with a corresponding spring 606 and, in the example shown, the force sensor 604 comprises a 3-point thin film resistive force sensor. In other examples, a separate force sensor 604 may be provided for each spring 606.

In the attachment 700 of FIG. 7, a switch-type sensor is provided for measuring the orientation of the skin-supporting rim 414 relative to the housing 302. The sensor in this embodiment comprises a first switch 702 located beneath the skin-supporting rim 414 one side of the pivot, and a second switch 704 located beneath the skin-supporting rim at an opposing side of the pivot. When a force is applied to one side of the skin-supporting rim 414 (e.g. as a result of the skin-supporting rim engaging the skin surface of a subject) nearest the first switch 702, the skin-supporting rim 414 is caused to pivot towards and engage the first switch, thereby activating the first switch. When a force is applied to the side of the skin-supporting rim 414 nearest the second switch 704, the skin-supporting rim 414 is caused to pivot towards and engage the second switch, thereby activating the second switch. Each skin-supporting rim 414 of the attachment is provided with a corresponding pair of switches, such that the orientation of each skin-supporting rim can be measured. One or both of the first and second switches 702, 704 may comprise a capacitive switch configured to react to (i.e. be activated by) the presence of (e.g. engagement with) the skin-supporting rim 414. By using the first and second switches 702, 704 for each skin-supporting rim 414, three orientations of each skin-supporting rim may be measured: a first orientation when the skin-supporting rim is tilted towards the first switch, a second orientation when the skin-supporting rim is tilted towards the second switch, and a third orientation when the skin-supporting rim is not tilted towards either switch, such that neither the first switch nor the second switch are activated.

Figure 8:
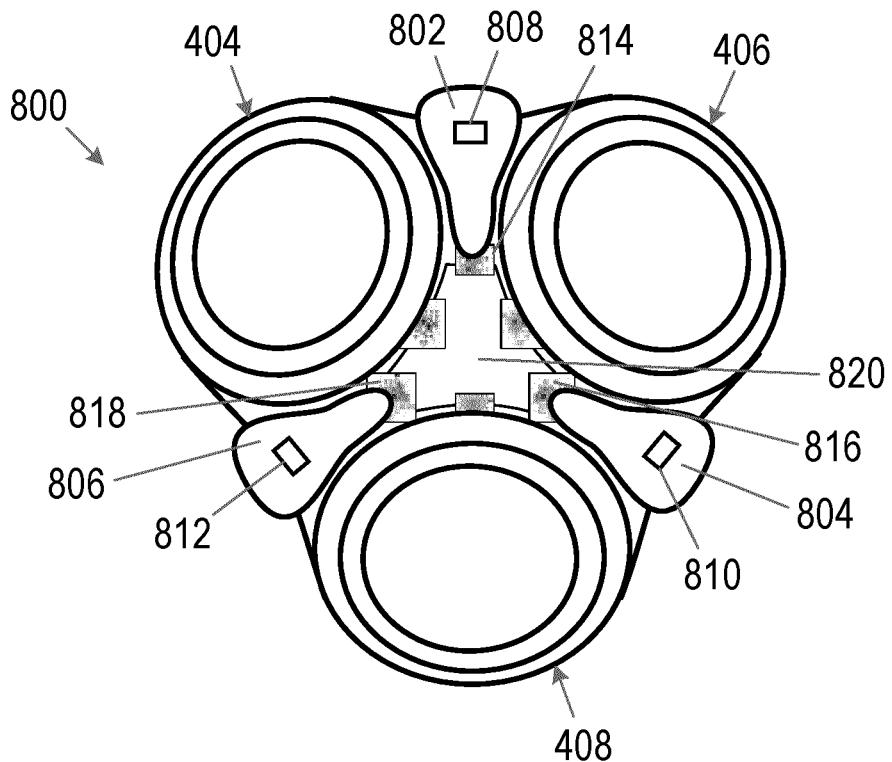
FIG. 8 is a plan view illustrations of an example of an attachment according to various embodiments.
Figure 9:
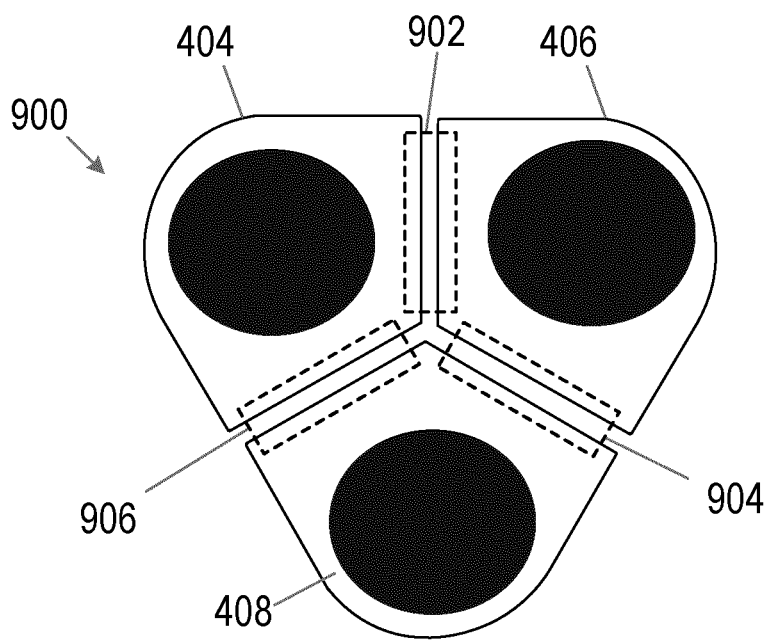
FIG. 9 is a plan view illustrations of a further example of an attachment according to various embodiments.

In the embodiments shown in FIGS. 6 and 7, the skin-supporting rim 414 of each treatment element 404, 406, 408 are the surface engaging elements whose orientation relative to the housing 302 is measured in order to determine the degree of curvature of the skin surface. However, in other embodiments, surface-engaging elements may be provided for curvature measurement, which are not part of the treatment element of the personal care device. FIGS. 8 and 9 are plan view illustrations of examples of attachments 800, 900 in which separate surface engaging elements are provided for measuring the curvature of the skin surface, in addition to the treatment elements for performing a personal care activity. In FIG. 8, surface-engaging elements 802, 804, 806 are provided between pairs of treatment elements 404, 406, 408. In this embodiment, each surface-engaging element 802, 804, 806 may be configured to pivot about a respective fulcrum 808, 810, 812, and compress a respective spring 814, 816, 818 as a force is applied to the surface-engaging element. Each spring 814, 816, 818 is in contact with a resistive force sensor 820, such that, as each spring is compressed, a resistance within the force sensor changes by an amount proportional to the applied force, and is measured by electronic components (not shown) in the attachment 800 or the personal care device to which is it attached. The arrangement of FIG. 8 functions in a manner similar to the arrangement shown in FIG. 6.

In some embodiments, the treatment elements 404, 406, 408 of FIG. 8 may also be arranged to pivot, as shown in the arrangements of FIGS. 6 and 7, such that the resistive force sensor 820 is able to measure an orientation of each treatment element in addition to the orientation of each surface-engaging element 802, 804, 806. In such an arrangement, additional curvature information (i.e. curvature information from the surface-engaging elements 802, 804, 806 and curvature information from the treatment elements 404, 406, 408) may be obtained as the personal care device is moved over the skin surface of a subject. In other examples, the surface-engaging elements 802, 804, 806 may be provided on a device having just one treatment element. Thus, curvature information may be measured on such a device, even though it may contain just one treatment element.

In an alternative embodiment, the skin surface curvature measurement mechanism comprises one or more flexible sensors comprising a plurality of capacitive sensors. In FIG. 9, an attachment 900 is shown having three treatment elements 404, 406, 408 which, in this example, may be treatment elements other than shaving units, such as brushes. The skin surface curvature measurement mechanism in this embodiment comprises three flexible sensors 902, 904, 906. Each flexible sensor 902, 904, 906 has a grid of capacitive sensors mounted thereon. In one example, electrodes (e.g. silver nanowires) are layered in a multi-layer stack on a flexible insulating substrate, with intermediate layers of polydimethylsiloxane (PDMS). When a skin-engaging element of each of the treatment elements 404, 406, 408 engage a skin surface, it pivots and engages one or more of the sensors 902, 904, 906, causing them to flex (e.g. as a result of a force being applied to the sensor). The surface of the electrodes is therefore caused to change, from which a measure of the curvature of the skin can be made. In other embodiments, fewer sensors of this type may be employed; for example, a single ring-shaped sensor made be provided, which is capable of determining a measure of the curvature of a skin surface with which it is in contact.

Figure 10:
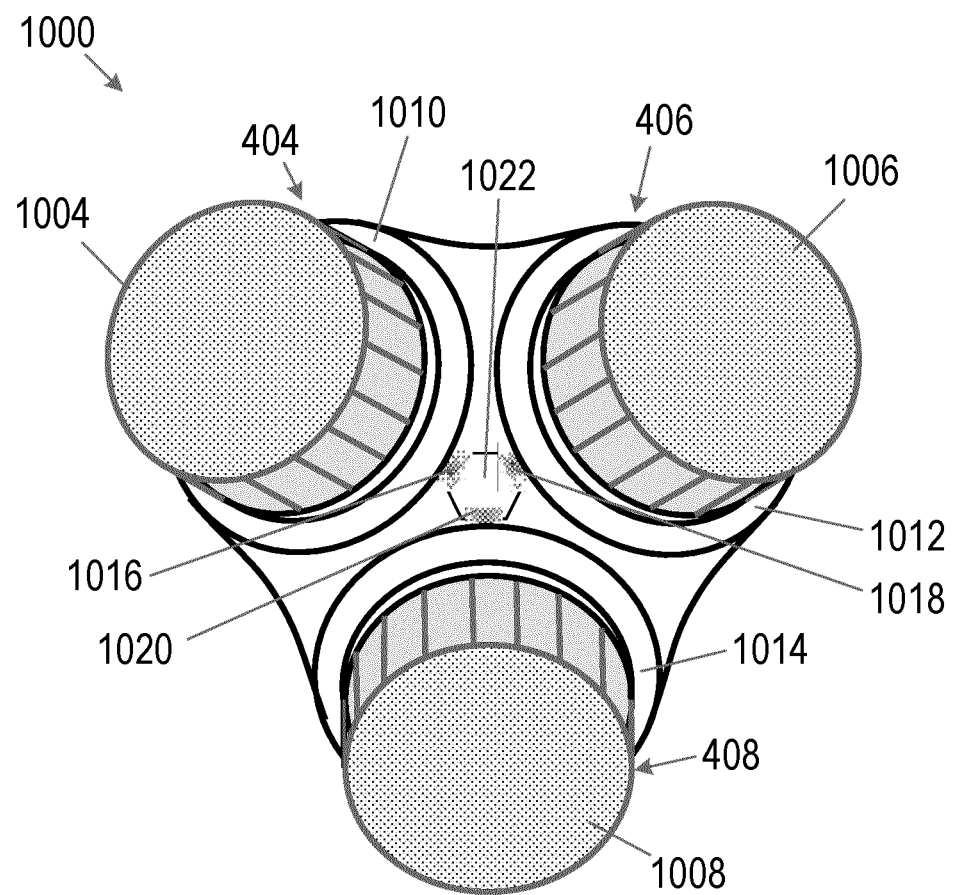
FIG. 10 is a plan view illustrations of a further example of an attachment according to various embodiments.

FIG. 10 is a plan view illustration of an attachment 1000 according to a further embodiment. In this embodiment, each treatment element 404, 406, 408 respectively comprises a rotatable brush 1004, 1006, 1008, for example for massaging or exfoliating a subject's skin. Each brush 1004, 1006, 1008 is rigidly mounted within a respective rim 1010, 1012, 1014, which is pivotally mounted to the housing 302, in a manner similar to the skin-supporting rim 414 of the attachments 600, 700 shown in FIGS. 6 and 7 respectively. A spring 1016, 1018, 1020 is positioned beneath one side of each rim 1010, 1012, 1014, such that, as a force is applied to that side of the brush, its respective rim 1010, 1012, 1014 is caused to pivot and compress the spring. The force applied to compress each spring is measured by a resistive force sensor 1022, in a manner similar to that discussed with reference to FIGS. 6 and 7.

Figure 11:
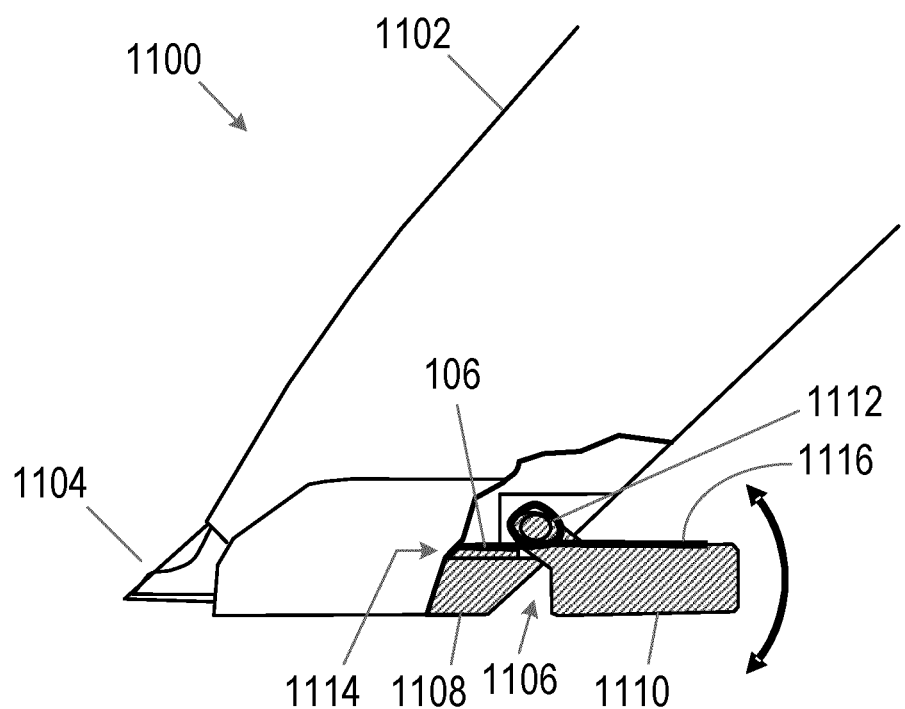
FIG. 11 is a side view illustration of a further example of a personal care device according to various embodiments.

FIG. 11 is a side view illustration of an example of a personal care device 1100 which, in this example, is a hair trimmer or clipper. The personal care device 1100 comprises a body 1102 which can be held by a user while a personal care activity (e.g. trimming or cutting hair) is performed. A treatment element 1104 is provided which, in this example, may comprise a blade or a pair or reciprocating blades configured to cut a hair that is encountered by the treatment element. The personal care device 1100 further comprises a skin surface curvature measurement mechanism 1106 which comprises a first surface-engaging element 1108 and a second surface-engaging element 1110 rotatable about a fulcrum 1112 relative to the first surface-engaging element. In this embodiment, the first surface-engaging element 1108 is in a fixed position relative to the body 1102, but the second surface-engaging element 1108 is able to pivot about the fulcrum 1112 in response to its engagement with the changing curvature of a skin surface of a subject with whom the personal care device 1100 is contact. Thus, in use, the treatment element 1104 and the first surface-engaging element 1108 engage a skin surface of the subject as the personal care device 1100 is moved over the skin surface. Data representative of the curvature, measured by the skin surface curvature measurement mechanism 1106, is processed using a processing apparatus 106 associated with the personal care device 1100, and a location of the personal care device with respect to the skin surface of the subject may be determined. In some embodiments, a sensor 1114 may be provided, and may form part of the skin surface curvature measurement mechanism 1106. The sensor 1114 is configured to measure an orientation of the first surface-engaging element 1108 relative to the second surface-engaging element 1110. In the example shown in FIG. 11, the sensor comprises a spring 1116 and a force sensor 1118 (e.g. a resistive force sensor). The spring 1116 is arranged to be bent or twisted as the second surface-engaging element 1110 pivots about the fulcrum 1112. The spring 1116 engages the force sensor 1118 such that, as the second surface-engaging element 1110 pivots and causes the spring to twist, the force applied by the spring on the force sensor changes relative to the change in relative orientations of the first and second surface-engaging element 1110. An indication of the force measured by the force sensor 1118 is received by the processing apparatus 106, which determines the location of the personal care device 1100 in the manner described herein.

Figure 12:
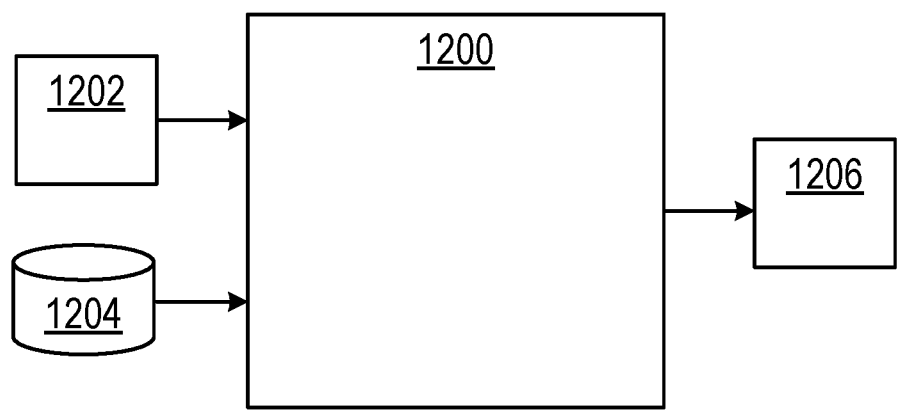
FIG. 12 is a schematic illustration of an example of a processing apparatus according to various embodiments.

In the embodiments described herein, the processing of data from the skin surface curvature measurement mechanism is performed by a processing apparatus or processor (e.g. the processing apparatus 106). According to a further aspect, the present invention provides such a processing apparatus. FIG. 12 is a schematic illustration of an example of a processing apparatus 1200 configured for determining a location of a personal care device with respect to a skin surface of a subject. The processing apparatus 1200 is configured to receive data 1202 representative of a measured degree of curvature of the skin surface within a first region of the skin surface of the subject, with which the personal care device is in contact. The data 1202 may, for example, be acquired using the skin surface curvature measurement mechanism 104, 1106 discussed above. The processing apparatus 1200 is further configured to retrieve, from a storage medium 1204, curvature information for a plurality of regions of the skin surface of the subject. The storage medium 1204 may, for example, comprise a memory storing a database or lookup table of curvature information for the plurality of regions of the skin surface of the subject. The processing apparatus 1200 is further configured to determine, by comparing the measured degree of curvature with the curvature information for the plurality of regions of the skin surface, a location of the first region of the skin surface on the subject, with which the personal care device is in contact. For example, if the curvature measured in the first region corresponds to curvature information in the storage medium that was obtained from a chin region, then it may be determined that the data representative of the measured degree of curvature was also obtained from the chin region of the subject. In some embodiments, the processing apparatus 1200 may also receive motion data for the personal care device, for example from a motion sensor, such as the sensor 206. The motion data may, for example, comprise data describing how the personal care device has been moved or displaced during a defined measurement period. The processing apparatus 1200 may be configured to determine the location of the first region of the skin surface on the subject further based on motion data. A sensor used to capture the motion data may be any sensor capable of measuring, amongst other things, a displacement of the personal care device and or, more specifically, displacement of the skin surface curvature measurement mechanism 104 of the personal care device. For example, the motion data may be acquired by an inertial measurement unit (IMU). The processing apparatus 1200 is further configured to generate, based on the determined location of the first region, an instruction 1206 of an action to be performed in respect of the personal care device. For example, the processing apparatus 1200 may generate an instruction (e.g. an instruction signal) to cause the personal care device to increase its power (e.g. cutting power) while it is located in the chin region. In other examples, the instruction of an action to be performed may comprise an instruction to provide feedback (e.g. via a user interface of the personal care device) to the subject regarding the personal care activity. In yet further examples, the instruction of an action to be performed may comprise an instruction to track parameters (e.g. skin parameters) over a period of time, for the provision of health and/or beauty advice.

Figure 13:
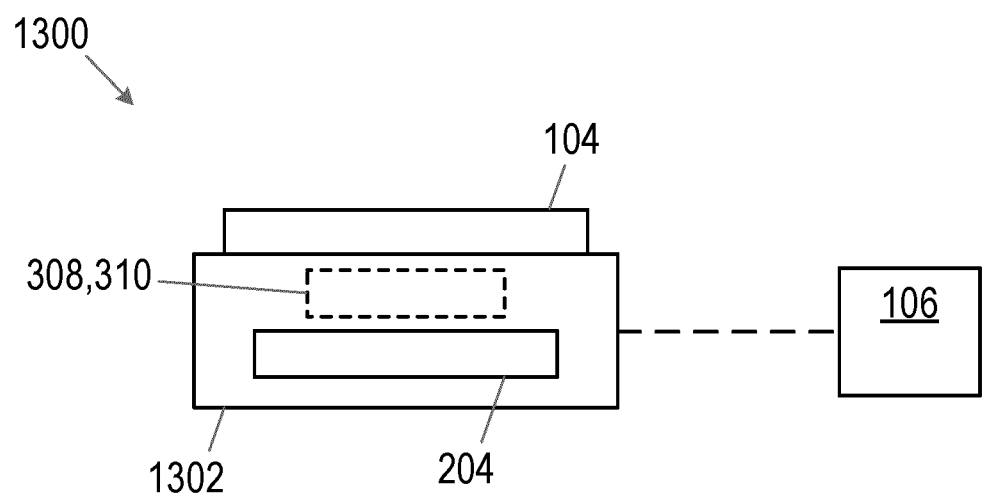
FIG. 13 is a schematic illustration of an example of a system according to various embodiments.

As noted previously, the attachment 202, 600, 700, 800, 900 may be detachable from a main body 102 of a personal care device. The attachment discussed herein may be considered to be a system in its own right. Thus, according to a further aspect, the present invention provides such a system. FIG. 13 is a schematic illustration of an example of a system 1300 for determining a location of a personal care device with respect to a skin surface of a subject. The system 1300 comprises a housing 1302 to house a communication unit 204. The system 1300 further comprises a skin surface curvature measurement mechanism 104 coupled to the housing 1302, the skin surface curvature measurement mechanism being configured for measuring a degree of curvature of the skin surface of the subject within a first region of the skin surface. The system 1300 further comprises a processing apparatus 106, 1200 as described herein. As discussed with reference to FIG. 12, the processing apparatus 106, 1200 is configured to receive data representative of a measured degree of curvature of the skin surface within a first region of the skin surface of the subject, with which the personal care device is in contact and, based on the data and other retrieved curvature information, determine a location of the first region.

The skin surface curvature measurement mechanism 104 is configured to generate the data representative of the measured degree of curvature of the skin surface within the first region of the skin surface. For example, the skin surface curvature measurement mechanism 104 may generate the data using techniques described herein. The communication unit 204 is configured to communicate the data representative of the measured degree of curvature of the skin surface within the first region of the skin surface to the processing apparatus 106, 1200. In some examples, the communication of the data between the communication unit 204 and the processing apparatus 106, 1200 may be achieved using known data transmission methods. For example, the communication unit 204 may transmit the data to a receiver associated with and/or connected to the processing apparatus 106, 1200.

The curvature of the skin surface may be measured in various ways using the skin surface curvature measurement mechanism 104. In some embodiments, as described above, the skin surface curvature measurement mechanism 104 may comprise a first surface-engaging element 305 and a second surface-engaging element 307 (see FIG. 3), and the first and second surface-engaging elements may be moveable relative to one another. In such examples, the data representative of the measured degree of curvature of the skin surface within the first region of the skin surface comprises a measure of a relative orientation of the first surface engaging element 305 and second surface engaging element 307.

In other embodiments, the curvature data may be measured in other ways. For example, in some embodiments, the skin surface curvature measurement mechanism 104 may comprise an imaging device configured to acquire image data in respect of the first region of the skin surface. For example, the imaging device may comprise a camera configured to capture an image or a series of images (e.g. a video stream) of the skin surface, from which the curvature of the skin surface can be measured or determined. In such embodiments, the processing apparatus 106, 1200 may be further configured to determine the degree of curvature of the skin surface within the first region of the skin surface using the acquired image data.

In embodiments in which the curvature data is acquired using a measurement of relative orientations of surface-engaging elements, rather than an imaging device, the system 1300 may comprise at least one orientation sensor 308, 310 configured for measuring an orientation of the first surface-engaging element 305 relative to the housing 1302, and an orientation of the second surface-engaging element 307 relative to the housing. Each of the at least one sensors 308, 310 may, in some embodiments, comprise a force sensor or a switch, as described in embodiments herein. The data representative of the measured degree of curvature of the skin surface within the first region of the skin surface may therefore comprise a measure of the orientation of the first surface-engaging element 305 relative to the housing 1302, and a measure of the orientation of the second surface-engaging element 307 relative to the housing.

In some embodiments of the system 1300, the first surface-engaging element 305 and the second surface-engaging element 307 are pivotally mounted such that they are each pivotable relative to the housing 1302 and relative to one another. For example, the first and second surface-engaging elements 305, 307 may be mounted in a manner similar to that shown in the embodiments of FIGS. 4 to 7.

The data representative of the measured degree of curvature may comprise an average degree of curvature of the skin surface within the first region. The average degree of curvature may be calculated from curvatures measured in multiple different 'directions' or normal planes as explained below. A curvature of a surface at a particular point is a measure of how the surface bends at that point. For example, at a point on the skin surface, consider a plane that contains the normal (outward) vector at that point. Such a normal plane cuts the skin surface in a plane curve. This curve will in general have different curvatures for different normal planes. The principal curvatures $k_{p1}$ and $k_{p2}$ are the maximum and minimum of these curvatures.

Examples of how a curvature (in one of the normal planes) at a point may be determined are discussed with reference to FIGS. 14 and 15. FIGS. 14A and 14B are diagrams showing how a curvature may be measured using skin surface curvature measurement mechanisms according embodiments disclosed herein. The examples shown in FIGS. 14A and 14B are based on a skin surface curvature measurement mechanism having a surface-engaging element 1400 similar to that shown in the embodiments of FIGS. 4 to 7. An axis at the center of the three treatment elements 404, 406, 408 (e.g. in the center of the housing 302 of FIG. 5), and perpendicular thereto (e.g. extending out of the page in FIG. 5) when the treatment elements are in their neutral, non-pivoted positions, is assumed to be an approximation of the normal to the skin surface at the center of the personal care device, when the personal care device is in use. Such a normal axis 1402 is indicated in FIGS. 14A and 14B. Now, consider a normal plane through this assumed surface normal and perpendicular to a pivot axis 1404 of the surface-engaging element 1400 (e.g. of one of the treatment elements 404, 406, 408). FIGS. 14A and 14B show such a normal plane 1406; the normal plane is the plane of the page. From an angle $\alpha_i$, which can be considered to represent the orientation of the skin surface normal at the center of the treatment element 1400 with respect to the skin surface normal 1402 at the center of the device, one can calculate a curvature $k_i$ (the reciprocal of the radius of curvature) as shown in FIGS. 14A and 14B. Curvature can be positive (as in FIG. 14A) or negative (as in FIG. 14B). In embodiments having three surface-engaging elements (e.g. of three treatment elements 404, 406, 408), three curvature values $k_1$, $k_2$, $k_3$ can be determined. An average degree of curvature ($k_{av}=\Sigma_i k_i/N$ where N is the number of surface-engaging elements) and a curvature range ($\Delta_k=$max/i $k_i$–min/i $k_i$) may be determined. The values of $k_{av}$ and $\Delta_k$ have an approximate relation to the principal curvatures according to the following relationships:

$$k_{av} \approx (k_{p1}+k_{p2})/2$$

$$\Delta_k \approx k_{p1}-k_{p2}$$

If the number of surface-engaging elements N is larger than 3, then values of $k_{av}$ and $\Delta_k$ are calculated using the above relationships. The relationship between $k_{av}$ and $\Delta_k$ and the principal curvatures may be more accurate when measurements are obtained from a greater number of surface-engaging elements.

In embodiments having just two surface-engaging elements (i.e. where N=2), the two pivot axes typically are aligned parallel to one another, and curvature is registered only in a single plane perpendicular to the pivot axes. In this case only $k_{av}$ is calculated.

In other embodiments where N=2, a single pivot axis may connect the two surface-engaging elements, as shown in the example of FIG. 15. In this example, which is based on the embodiments of FIG. 11, a first surface-engaging element 1500 and a second surface-engaging element 1502 are pivotally connected to a fulcrum 1504. In this example, a bisector 1506 that divides the opening angle into to equal halves may be taken as the assumed normal axis to the skin surface, as indicated in FIG. 15. According to a further aspect, a computer-implemented method is provided.

Figure 16:
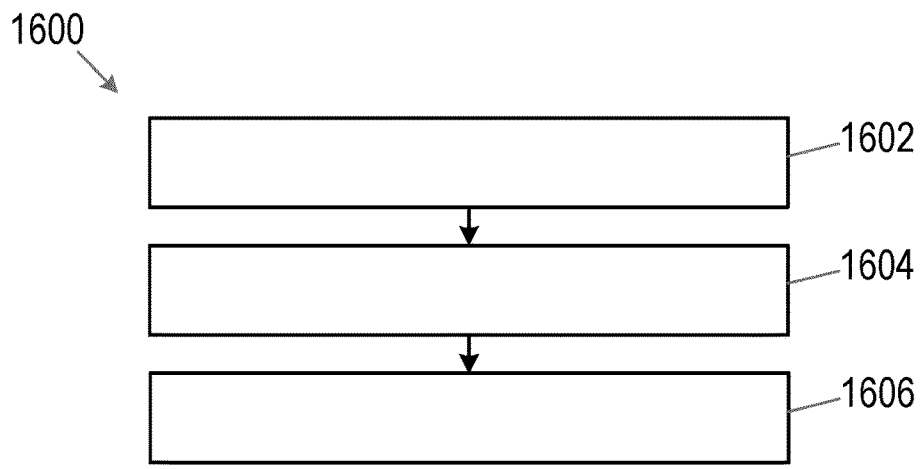
FIG. 16 is a flowchart of an example of a computer-implemented method of determining a location of a personal care device with respect to a skin surface of a subject according to various embodiments.

FIG. 16 is a flowchart of an example of a computer-implemented method 1600 of determining a location of a personal care device with respect to a skin surface of a subject. The method 1600 comprises, at step 1602, receiving data representative of a measured degree of curvature of the skin surface within a first region of the skin surface of the subject, with which the personal care device is in contact. The received data may, for example, be acquired or measured using a skin surface curvature measurement mechanism 104, 1106 and/or using techniques described herein. For example, as a user moves the personal care device over the surface of their skin, the data may be measured and received by a processor or processing apparatus performing the method 1600. At step 1604, the method 1600 discloses determining, by comparing the measured degree of curvature with curvature information for a plurality of regions of the skin surface of the subject contained in a database, an indication of a location of the first region of the skin surface on the subject. The method 1600 comprises, at step 1606, performing, based on the determined indication of the location of the first region, an action in respect of the personal care device. The action to be performed depends on the nature of the personal care device. In some examples, the action performed may include adjusting an operating parameter of the personal care device, such as a motor speed, or a cutting length of a blade.

Figure 17:
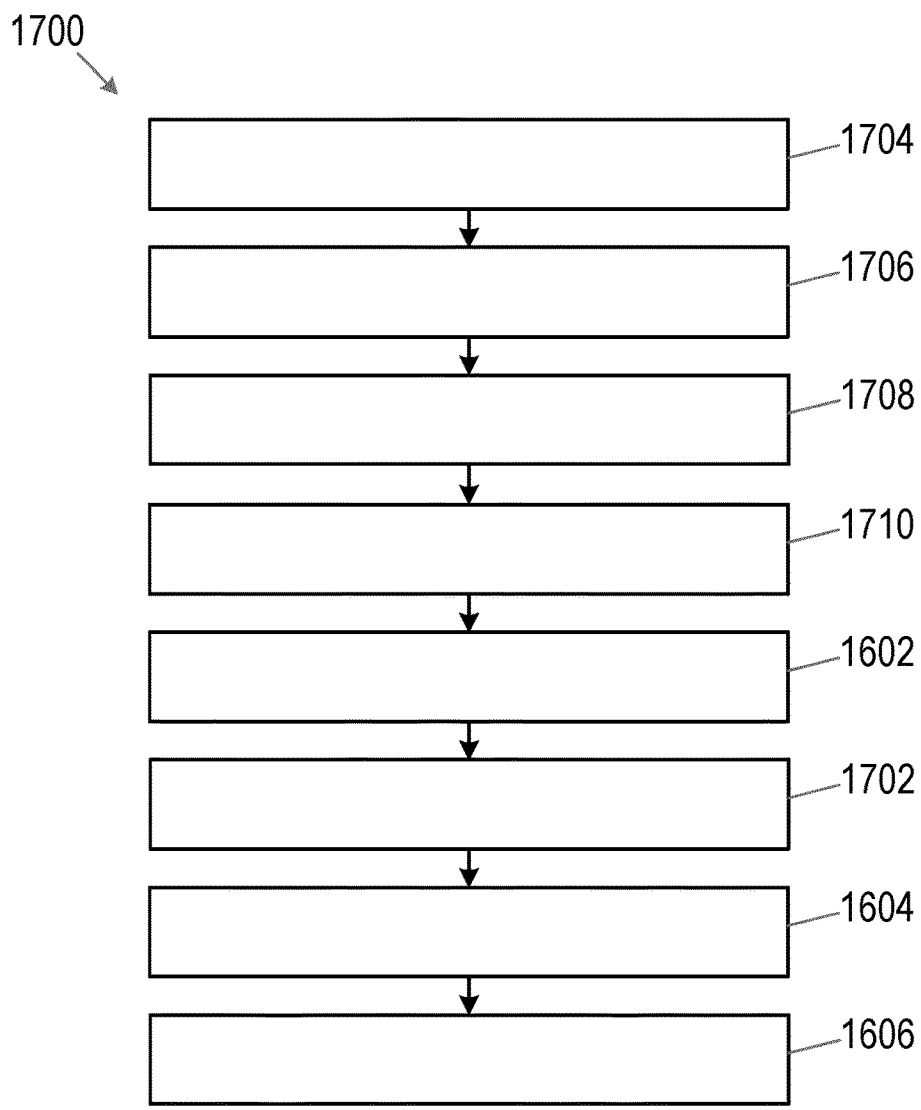
FIG. 17 is a flowchart of a further example of a computer-implemented method of determining a location of a personal care device with respect to a skin surface of a subject according to various embodiments.

As noted above, the location of the personal care device with respect to the skin surface (i.e. the location of the first region) may be determined more accurately when data indicative of the motion of the personal care device is also taken into account. Thus, a motion sensor, such as an IMU may be provided in the personal care device and used to measure the movement of the device. FIG. 17 is a flowchart of a further example of a method 1700 of determining a location of a personal care device with respect to a skin surface of a subject. The method 1700 includes the steps 1602, 1604 and 1606 of FIG. 16. In some embodiments, the method 1700 may further comprise, at step 1702, receiving data indicative of a measured displacement of the personal care device between the first region of the skin surface and a second region of the skin surface, with which the personal care device was previously in contact. Thus, the displacement may be measured using the motion sensor, such as the IMU, and may provide information indicating a previous location from which the device has moved. In one example, the data may indicate that a personal care device such as a shaver has been moved from the second region to the first region in a movement representative of a move from the top of the subject's chin to the top right part of the subject's chin. In such examples where data indicative of a measured displacement is available, determining the indication of the location of the first region may further be based on comparing the data indicative of a measured displacement with position information for the plurality of regions of the skin surface of the subject contained in the database. Thus, if is it determined the data indicative of a measured displacement corresponds to position information (e.g. previously-acquired data indicating two positions, or the movement between the two positions), then that determination may help to reinforce the determination of the location of the first region made using the curvature data from the skin surface curvature measurement mechanism.

The curvature information that is compared in step 1604 with the data received in step 1602 may be acquired during a calibration process performed by the subject prior to use of the personal care device, or during its first use. In some embodiments, the method 1700 may further comprise a series of steps prior to receiving (at step 1602) the data representative of the measured degree of curvature of the skin surface within the first region of the skin surface. At step 1704, the method 1700 may comprise receiving calibration displacement data indicative of a displacement of the personal care device between a plurality of regions of the skin surface of the subject. The calibration displacement data indicative of the displacement may, for example, be received during a calibration process as discussed above, using the motion sensor (or calculated from data acquired using the motion sensor) of the personal care device in the manner disclosed herein. When the personal care device is to be used by a user for the first time, the user may be prompted to perform a calibration. Each user of the personal care device may, for example, perform a personalized calibration of the personal care device by moving the device over their skin (or a portion thereof) the first time they use the device, so that the calibration displacement data indicative of the displacement can be measured. Measured calibration displacement data for a subject may be stored in association with the subject, for example as part of a user profile. In some embodiments, a user may be prompted to start the calibration process with the personal care device in a particular position, such as on their chin, to provide a defined reference to the location of the personal care device during the calibration. In some examples, curvature data may also be acquired during the calibration process (e.g. using the skin surface curvature measurement mechanism) and, in such examples, the curvature data may also be stored in association with the data representative of the displacement.

During the calibration, as the personal care device is moved, data indicative of a measured displacement (e.g. from the IMU) may be recorded in terms of the displacement of the personal care device in three dimensions (e.g. $\Delta x$, $\Delta y$, $\Delta z$). The skin surface curvature measurement mechanism measures data representative of a curvature of the skin surface as the personal care device is moved over the skin surface, providing orientation data ($\alpha_1, \ldots, \alpha_2$). From the data indicative of a measured displacement, the processing apparatus is able to calculate a current position of the device relative to a position of the device when the data collection started. From the orientation data, values representing curvature of the skin surface can be calculated, as discussed above. The relative position data is stored in the storage medium (e.g. the memory) together with the concurrently obtained curvature values. Data sampling and processing in this way may continue until a defined amount of data has been acquired, or until the calibration process is otherwise ended. In other embodiments, data indicative of a measured displacement (e.g. from an IMU) may not be acquired, and the calibration of the personal care device may be performed based just on the orientation data from the skin surface curvature measurement mechanism.

In some embodiments, at the end of the calibration process (e.g. indicated by the user pressing a button on the personal care device or by the expiration of a predefined amount of time), the processing apparatus may be configured to determine whether or not a sufficient amount of data has been acquired. For instance, the processing apparatus may be configured to determine whether the spatial extent of the subject's skin surface that has been covered fits within expected minimum and maximum boundaries. If it is determined that the data is incomplete (e.g. that more data is required from the calibration), then the user may be asked to repeat or supplement the calibration process either immediately or at a later time.

If, on the other hand, it is determined that the amount and/or quality of data acquired is complete and/or adequate, then the method 1700 may proceed to a model fitting step. Thus, the method 1700 may further comprise, at step 1706, fitting a computer model of the skin surface of the subject to the received calibration displacement data indicative of the displacement of the personal care device. The processing apparatus may, for example, be configured to fit a model (e.g. a face model) to the stored relative position data. The face model may, for example, be a general CAD-like model of a human face controlled by a set of model parameters that determine the distances between facial landmarks (e.g. the chin, corners of the mouth, ears, jaw angles, and the like) and the shape of facial elements (e.g. flatter or rounder cheeks, neck, and the like). In other examples, the model may comprise a model of another part of the subject's body.

At the start of the model fitting process, a coronal plane (i.e. a plane dividing a subject's face between a left side and a right side) and the chin may be identified in a "point cloud" formed by the relative position data. In some embodiments, machine learning techniques may be applied to aid the identification. The face model (which may be provided with model parameters based on average or arbitrary values) may be aligned to the coronal plane and the chin identified in the relative position data. In some embodiments, the alignment process may involve applying a least squares fit process. In such a process, for each point in the relative position data, the distance to the surface of the face model may be calculated. The sum of the squares of these distances provides a measure for the goodness of the fit of the model to the measured position data, for the current model parameters. The model parameters may then be adapted by an optimization algorithm until the sum of squares is reduced or minimized. A good optimization algorithm may converge to a global minimum, which represents the best possible fit of the model to the measured data. For embodiments where the personal care device comprises a beard trimmer or shaver, only the lower part of the face model (below the nose-ear line) and related model parameters may be used. Thus, the method 1700 may further comprise, at step 1708, determining, from the calibration displacement data and the fitted computer model, curvature information for each region of the plurality of regions.

In some examples, curvature information may be estimated from the fitted model. For example, it may be clear from a point cloud of displacement data which parts of the data correspond to certain parts of the subject's body or face, and curvature information may be known or predetermined for those areas. In other examples, curvature information may be acquired along with the calibration displacement data, and the curvature information may be stored in association with the corresponding calibration displacement data.

For a selected number of points on the fitted face model, a set of corresponding curvature values may be calculated (e.g. via interpolation and averaging of the curvature values linked to the nearest relative position data). The fitted model and corresponding curvature values may then be stored in the memory. Thus, at step 1710, the method 1700 may further comprise storing, in the database, the determined curvature information in association with the corresponding region on the skin surface of the subject.

Steps of the methods 1600, 1700 may be performed using the processing apparatus 106, 1200 described herein.

Figure 18:
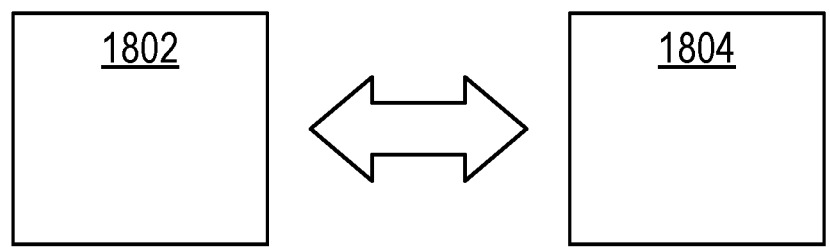
FIG. 18 is a schematic illustration of a computer-readable medium in communication with a processor.

According to a further aspect, the invention provides a computer program product. FIG. 18 is a schematic illustration of an example of a computer-readable medium 1804 in communication with a processor 1802. According to some embodiments, a computer program product comprises a non-transitory computer-readable medium 1804, the computer-readable medium having computer-readable code embodied therein, the computer-readable code being configured such that, on execution by a suitable computer or processor 1804, the computer or processor is caused to perform steps of the method 1600, 1700 disclosed herein. The processor 1802 may comprise, or function in a manner similar to the processing apparatus 106, 1200.

The processor or processing apparatus 106, 1200, 1802 can comprise one or more processors, processing units, multi-core processors or modules that are configured or programmed to control the system 1300 in the manner described herein. In particular implementations, the processor or processing apparatus 106, 1200, 1802 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at runtime. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of determining a location of a personal care device with respect to a skin surface of a subject, the personal care device being configured to perform a personal care treatment to the skin when in contact with the skin surface, the method comprising:
   receiving data representative of a measured degree of curvature of the skin surface within a first region of the skin surface of the subject, with which the personal care device is in contact;
   determining, by comparing the measured degree of curvature with curvature information for a plurality of regions of the skin surface of the subject contained in a database, an indication of a location of the first region of the skin surface on the subject; and
   performing, based on the determined indication of the location of the first region, an action in respect of the personal care device.

2. The method according to claim 1, further comprising:
   receiving data indicative of a measured displacement of the personal care device between the first region of the skin surface and a second region of the skin surface, with which the personal care device was previously in contact;
   wherein determining the indication of the location of the first region is based further on comparing the data indicative of the measured displacement with position information for the plurality of regions of the skin surface of the subject contained in the database.

3. The method according to claim 1, further comprising:
   prior to receiving the data representative of the measured degree of curvature of the skin surface within the first region of the skin surface:

receiving calibration displacement data indicative of a measured displacement of the personal care device between a plurality of regions of the skin surface of the subject;

fitting a computer model of the skin surface of the subject to the received calibration displacement data;

determining, from the calibration displacement data and the fitted computer model, curvature information for each region of the plurality of regions; and storing, in the database, the determined curvature information in association with the corresponding region on the skin surface of the subject.

4. A non-transitory computer readable medium having computer readable code embodied therein, the computer readable code being configured such that, on execution by a suitable computer or processor, the computer or processor is caused to perform the method of claim 1.

5. A processing apparatus configured for determining a location of a personal care device with respect to a skin surface of a subject, the personal care device being configured to perform a personal care treatment to the skin when in contact with the skin surface, the processing apparatus being configured to:

receive data representative of a measured degree of curvature of the skin surface within a first region of the skin surface of the subject, with which the personal care device is in contact;

retrieve, from a storage medium, curvature information for a plurality of regions of the skin surface of the subject;

determine, by comparing the measured degree of curvature with the curvature information for the plurality of regions of the skin surface, a location of the first region of the skin surface on the subject; and generate, based on the determined location of the first region, an instruction of an action to be performed in respect of the personal care device.

6. A system for determining a location of a personal care device with respect to a skin surface of a subject, the personal care device being configured to perform a personal care treatment to the skin when in contact with the skin surface, the system comprising:

a housing to house a communication unit;

a skin surface curvature measurement device coupled to the housing, the skin surface curvature measurement device being configured for measuring a degree of curvature of the skin surface of the subject within a first region of the skin surface; and the processing apparatus according to claim 5;

wherein the skin surface curvature measurement device is configured to generate the data representative of the measured degree of curvature of the skin surface within the first region of the skin surface; and wherein the communication unit is configured to communicate the data representative of the measured degree of curvature of the skin surface within the first region of the skin surface to the processing apparatus.

7. The system according to claim 6, wherein the skin surface curvature measurement device comprises an imaging device configured to acquire image data in respect of the first region of the skin surface; and wherein the processing apparatus is further configured to determine the degree of curvature of the skin surface within the first region of the skin surface using the acquired image data.

8. The system according to claim 6, wherein the skin surface curvature measurement device comprises a first surface-engaging element and a second surface-engaging element, the first and second surface-engaging elements being moveable relative to one another; and wherein the data representative of the measured degree of curvature of the skin surface within the first region of the skin surface comprises a measure of a relative orientation of the first surface-engaging element and second surface-engaging element.

9. The system according to claim 8, further comprising:

at least one orientation sensor configured for measuring an orientation of the first surface-engaging element relative to the housing, and an orientation of the second surface-engaging element relative to the housing;

wherein the data representative of the measured degree of curvature of the skin surface within the first region of the skin surface comprises a measure of the orientation of the first surface-engaging element relative to the housing and a measure of the orientation of the second surface-engaging element relative to the housing.

10. The system according to claim 8, wherein the first surface-engaging element and the second surface-engaging element are pivotally mounted such that they are each pivotable relative to the housing and relative to one another; and wherein the data representative of the measured degree of curvature comprises an average degree of curvature of the skin surface within the first region.

11. A personal care device configured to perform a personal care treatment to the skin when in contact with the skin surface, comprising:

a main body;

a skin surface curvature measurement mechanism, the skin surface curvature measurement mechanism being configured for measuring a degree of curvature of the skin surface of the subject within a first region of the skin surface, with which the personal care device is in contact; and the processing apparatus according to claim 5, the processing apparatus configured to receive data representative of a measured degree of curvature of the skin surface from the skin surface curvature measurement mechanism.

12. The personal care device according to claim 11, further comprising:

an attachment to house a communication unit, the attachment being detachably mountable to the main body;

wherein the skin surface curvature measurement mechanism is coupled to the attachment;

wherein the main body accommodates the processing apparatus;

wherein the communication unit is configured to communicate the data representative of the measured degree of curvature of the skin surface to the processing apparatus.

13. The personal care device according to claim 11, further comprising:

a sensor for acquiring motion data for the personal care device;

wherein the processing apparatus is configured to determine the location of the first region of the skin surface on the subject further based on motion data acquired using the sensor.

14. The personal care device according to claim 11, further comprising:

a housing supporting at least a first treatment element and a second treatment element;

wherein the first treatment element comprises a first surface-engaging element, and the second treatment element comprises a second surface-engaging element, the first surface-engaging element and the second surface-engaging element each being pivotally mounted relative to the housing such that they are pivotable relative to one another; and wherein the skin surface curvature measurement device comprises a first sensor configured to measure an orientation of the first surface-engaging element relative to the housing and a second sensor configured to measure an orientation of the second surface-engaging element relative to the housing.

15. The personal care device according to claim 14, wherein the personal care device is an electric shaver, wherein the first treatment element and the second treatment element both comprise a shaving unit having an external cutting member, an internal cutting member movably arranged relative to the external cutting member, and a skin-supporting rim surrounding the external cutting member and pivotally mounted relative to the housing, wherein the first surface-engaging element and the second surface-engaging element comprise the skin-supporting rim of the shaving unit of, respectively, the first treatment element and the second treatment element.

* * * * *